(12) United States Patent
Fournet, II

(10) Patent No.: US 8,100,847 B2
(45) Date of Patent: Jan. 24, 2012

(54) PROTECTIVE SKIN COVER

(76) Inventor: Louis J. Fournet, II, Franklin, LA (US)

( * ) Notice: Subject to any disclaimer, the term of this patent is extended or adjusted under 35 U.S.C. 154(b) by 544 days.

(21) Appl. No.: 12/286,848

(22) Filed: Oct. 2, 2008

(65) Prior Publication Data

US 2009/0112143 A1  Apr. 30, 2009

Related U.S. Application Data

(60) Provisional application No. 61/000,230, filed on Oct. 25, 2007.

(51) Int. Cl.
*A61F 13/00* (2006.01)

(52) U.S. Cl. .......... 602/61; 602/3; 602/41; 602/42; 602/43; 602/62; 602/63

(58) Field of Classification Search .......... 128/888, 128/889, 882; 602/41–65, 3
See application file for complete search history.

(56) References Cited

U.S. PATENT DOCUMENTS

| | | | |
|---|---|---|---|
| 4,519,798 A * | 5/1985 | Dinius | 604/358 |
| 4,959,059 A * | 9/1990 | Eilender et al. | 604/358 |
| 5,899,207 A | 5/1999 | Scheinberg | |
| 6,067,987 A | 5/2000 | Scheinberg | |
| 6,070,273 A | 6/2000 | Sgro | |
| 7,181,722 B2 | 2/2007 | Gillen et al. | |
| 2006/0277641 A1 | 12/2006 | Gazaui | |
| 2007/0119462 A1 | 5/2007 | Shumate, Sr. et al. | |

* cited by examiner

*Primary Examiner* — Kim M Lewis
(74) *Attorney, Agent, or Firm* — Ted M. Anthony

(57) ABSTRACT

A protective skin covering has at least three distinct layers that can be worn on multiple parts of the human body. An inner layer substantially surrounds an area over which a protective skin covering is to be worn, and is constructed of soft, non-abrasive fabric. A middle layer provides padding to protect a wearer against impact with foreign objects. An outer layer is a durable, flexible, material (such as, for example, nylon or other similar material) that protects the middle layer, protects the skin of the wearer, resists wear and tear, and provides a surface for decorative designs or other attractive features.

13 Claims, 3 Drawing Sheets

PROTECTIVE SKIN COVER

CROSS REFERENCES TO RELATED APPLICATION

This application is related to and claims priority from U.S. Provisional Patent Application No. 61/000,230 filed Oct. 25, 2007, which is hereby incorporated by reference.

STATEMENTS AS TO THE RIGHTS TO THE INVENTION MADE UNDER FEDERALLY SPONSORED RESEARCH AND DEVELOPMENT

NONE

BACKGROUND OF THE INVENTION

1. Field of the Invention

The present invention relates to a protective skin cover. More particularly, this invention relates to a protective apparatus for covering exposed skin, especially for use by individuals having thin or damaged skin.

2. Brief Description of the Prior Art

Skin can become damaged from a variety of different causes. For example, exposure to ultra-violet ("UV") radiation, toxic chemicals and/or heat can cause skin damage or thinning. In many cases, such skin damage or thinning can increase with advanced age. By way of illustration, but not limitation, dermatoheliosis (also commonly referred to as "photo-aging") is a skin condition resulting from prolonged exposure to sunlight over an extended period of time. Dermatoheliosis, as well as numerous other skin conditions, can cause skin to become damaged, thinner and/or more susceptible to puncturing or tearing.

Individuals having thin and/or damaged skin are especially susceptible to skin tearing and bruising (and sometimes accompanying bleeding and infection) when such skin comes in contact with foreign objects, even when such contact is minor or incidental. Such tearing and other injuries often occur on hands, forearms and other extremities that frequently or inadvertently strike or contact foreign objects. Such tearing and other injuries can be painful, unsightly and difficult to prevent, and can cause individuals to become extremely self-conscious about their appearance. Further, such tearing and other injuries can also lead to other more serious medical conditions, especially on areas such as the back of the hand or the forearms that are at risk of repeated and/or inadvertent contact with foreign objects.

Several prior art arm protectors have been designed to protect the forearm area, especially for individuals taking blood thinners or who are particularly susceptible to bruising. While these prior art protectors offer some defense against exposure to sunlight and/or protection against inadvertent contact with foreign objects, none of these existing devices are capable of being used with damaged (internally or externally) or compromised skin. Further, many of said prior art devices utilize a layer of leather or other relatively heavy and non-porous material that can irritate the skin, traps moisture (such as, for example, perspiration), and is uncomfortable and difficult to clean. While such prior art devices may be acceptable for those using blood thinners or the like, such prior art devices do not work well for those suffering from internally or externally damaged skin.

Accordingly, a need exists for a lightweight, reusable and effective protective skin cover that can be worn by individuals having thin or damaged skin. The protective skin cover should be attractive, comfortable and easy to use, and should protect exposed skin from ultra-violet radiation and/or other harmful substances or effects.

SUMMARY OF THE PRESENT INVENTION

The present invention comprises a protective skin covering having multiple distinct layers. The protective skin covering of the present invention can be fashioned in any number of different configurations that can be worn on multiple parts of the human body. Accordingly, the specific configurations described herein are illustrative only, and are not intended to represent an exhaustive list of all possible configurations or designs of the present invention, or all parts of the human body that could benefit from the protective skin covering of the present invention.

In the preferred embodiment, the protective skin covering of the present invention comprises three distinct layers: an inner layer (disposed directly against the skin of a user), a middle layer, and an outer layer.

The inner layer of the present invention substantially surrounds the area over which said protective skin covering is to be worn, and is constructed of soft, non-abrasive fabric. In the preferred embodiment, the fabric of said inner layer is hypoallergenic and anti-bacterial, and beneficially exhibits superior "wicking ability", such that moisture (including, but not limited to, perspiration) is drawn away from a wearer's skin. Further, said inner layer is sewn so that seams are positioned on the outer surface of such inner layer—and away from the skin—to further prevent skin irritation or abrasion.

The middle layer of the present invention provides padding to protect a wearer against impact with foreign objects. Said middle layer generally comprises foam or cushioning material, the thickness of which is typically dictated by the part of the body that is being protected by the skin covering of the present invention. For example, said middle layer may be beneficially thicker when placed in proximity to parts of the body having little or no muscle tissue. Such middle layer also exhibits superior "wicking ability," especially compared to prior art leather or plastic protective layers.

The outer layer of the present invention typically comprises a durable, flexible, material (such as, for example, nylon or other similar material). In the preferred embodiment, said outer layer represents a surface for decorative designs or other attractive features. Said outer layer also protects said middle layer, resists wear and tear, and provides a durable shield to protect skin from contact with foreign objects.

In the preferred embodiment of the present invention, said outer layer is directly affixed or joined to said middle layer only at or near the edges of said middle layer. Further, said inner layer is likewise attached or connected to said middle layer 30 only at or near the outer perimeter of said middle layer 30. As a result, the middle layer of the present invention can slide or move laterally relative to said inner and outer layers when a foreign object makes contact with the outer surface.

In the preferred embodiment, the protective skin covering of the present invention is lightweight, inexpensive, and fully washable. Further, said protective skin covering can be easily folded or rolled for convenient storage and/or portability. Said protective skin covering can be used to safely protect damaged or sensitive skin during any number of different activities including, without limitation, every-day activities, and can be worn comfortably for extended periods of time (even all day, if so desired). Although not desirable as a reusable bandage due to its absorbent quality, the present invention can be used to secure a bandage or other dressing on a wound when surrounding skin is too thin or damaged for the use of adhesive tape.

BRIEF DESCRIPTION OF THE DRAWINGS

The foregoing summary, as well as the following detailed description of the preferred embodiments, is better understood when read in conjunction with the appended drawings. For the purpose of illustrating the invention, the drawings show certain preferred embodiments. It is understood, however, that the invention is not limited to the specific methods and devices disclosed.

DETAILED DESCRIPTION OF A PREFERRED EMBODIMENT OF THE INVENTION

Figure 1:
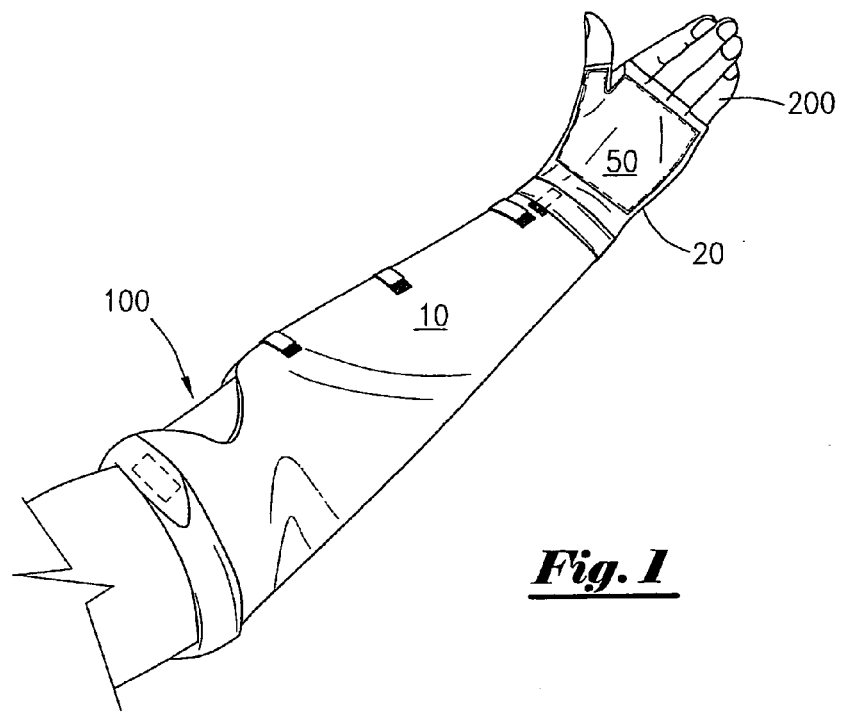
FIG. 1 depicts an overhead perspective view of articles constructed of the protective skin covering of the present invention being worn on a forearm and hand of a user.

Referring to the drawings, FIG. 1 depicts an overhead perspective view of articles 10 and 50 constructed of the protective skin covering of the present invention. Protective skin covering 10 is depicted being worn on right arm 100 of a user, while glove-like protective covering 50 is depicted being worn on right hand 200 of a user.

Figure 2:
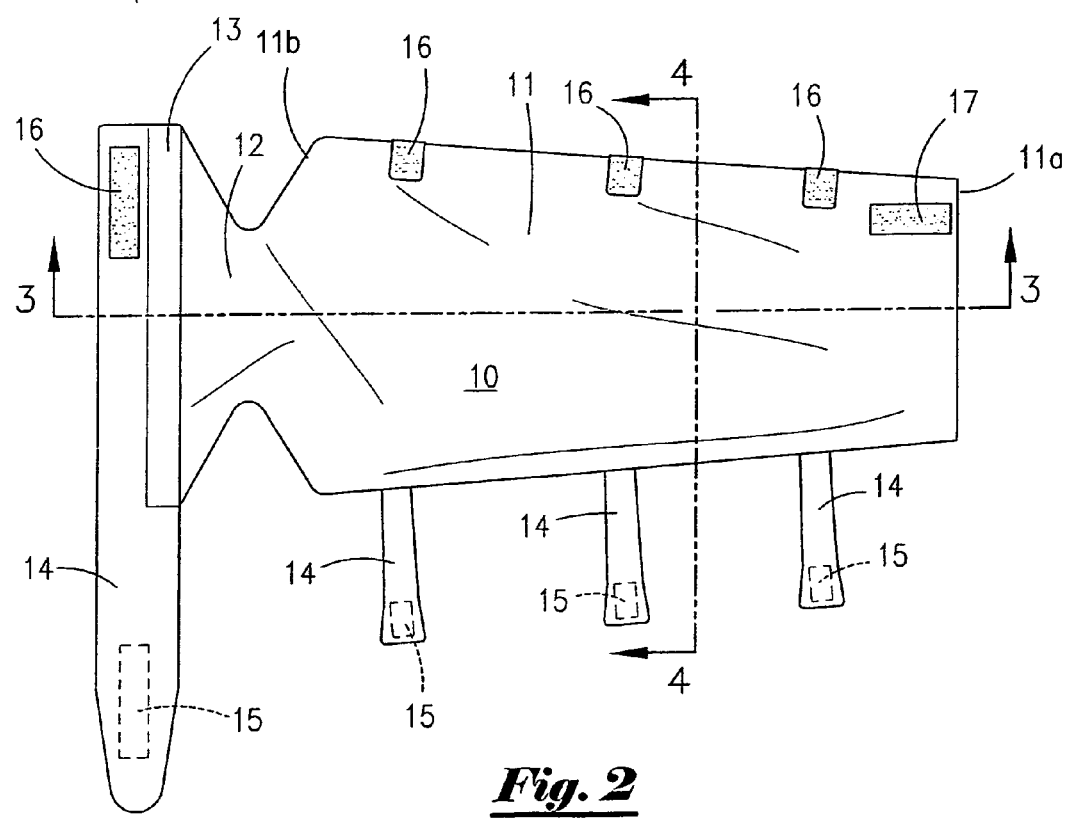
FIG. 2 depicts a top view of an opened protective skin covering of the present invention for use on a forearm.

FIG. 2 depicts a top view of protective skin covering 10 of the present invention for use on a right arm, such as arm 100 in FIG. 1. People having thin or damaged skin are especially susceptible to skin tears and bruising (and sometimes accompanying bleeding and infection) when such skin contacts foreign objects, even when such contact is relatively minor. Such tearing and other injuries often occur on portions of the body that frequently or inadvertently strike or contact foreign objects, such as forearms.

Protective skin covering 10 is beneficially sized to accommodate an arm of a user. Specifically, lower sleeve section 11, having forward end 11a and back end 11b, is generally sized to fit over and substantially cover the forearm of a user. As such, lower sleeve section 11 is of sufficient length to span substantially the entire distance from a user's elbow area to said user's wrist area. Further, in the preferred embodiment, lower sleeve section 11 extends around the entire circumference of a user's forearm. In the preferred embodiment, sleeve section 11 is narrower at its forward end 11a (which, when in use, is positioned in proximity to a user's wrist) and wider at its back end 11b (which, when in use, is positioned in general proximity to a user's elbow) to accommodate changes in thickness of a user's forearm area.

Still referring to FIG. 2, flap 12 is connected to back end 11b of sleeve section 11. In the preferred embodiment, flap 12 tapers inward toward its center and is narrower than back end 11b of sleeve section 11. When worn by a user, flap 12 is positioned in general alignment with the outer surface of user's elbow area. Upper strap 13 is connected to flap 12. When in use, upper strap 13 is positioned in proximity to the base of a user's upper arm or bicep area.

In the preferred embodiment, a plurality of lower straps 14 is disposed along one side of said sleeve section 11. Fastening means are provided to selectively secure protective skin covering 10 to the arm of a user, and control the tightness of said skin covering 10 on said arm. In the preferred embodiment, said fastening means comprise hook and loop fasteners (such as Velcro® brand fasteners) that are well known in the art. Hook members 15 are disposed on the under side of lower straps 14, as well as upper strap 13. Mating loop members 16 are disposed on the outer surface of sleeve section 11 and upper strap 13. Upper strap 13 and lower straps 14 can be selectively loosened or tightened to adjust the grip of said protective skin covering on a user's arm.

Figure 3:
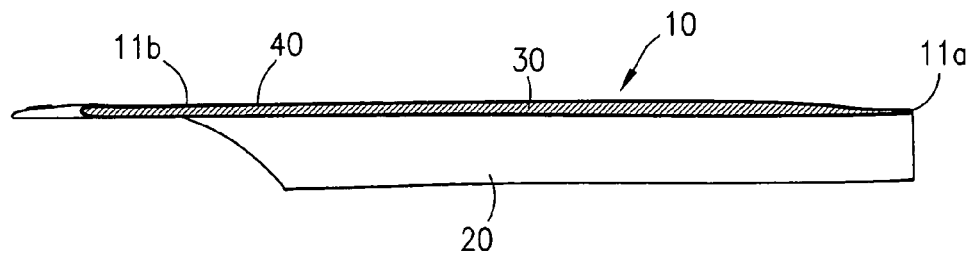
FIG. 3 depicts a cross-sectional view of the protective skin covering of the present invention depicted in FIG. 2 along line 3-3 of FIG. 2.

FIG. 3 depicts a cross-sectional view of protective skin covering 10 of the present invention depicted in FIG. 2 along line 3-3 of FIG. 2. In the preferred embodiment, protective skin covering 10 of the present invention comprises three distinct layers: inner layer 20 (which is disposed directly against the skin of a user), middle layer 30, and outer layer 40.

Inner layer 20 of protective skin covering 10 of the present invention forms a sleeve that substantially surrounds a user's forearm, and is constructed of soft, non-abrasive fabric. The fabric of said inner layer 20 is hypoallergenic and anti-bacterial, and beneficially exhibits superior "wicking ability," such that moisture (including, but not limited to, perspiration) is drawn away from a user's skin. Said inner layer 20 is beneficially constructed so that seams are positioned or oriented on the outer surface of such inner layer 20 to further prevent skin irritation and abrasion. In the preferred embodiment, said inner layer 20 of skin covering 10 is constructed of fabric made from bamboo fiber; however, it is to be observed that any material having desired characteristics can be used to construct said inner layer 20.

Middle layer 30 of the present invention comprises padding that serves to cushion a user's forearm from impact with foreign objects. In the preferred embodiment, said middle layer 30 generally comprises foam (including, without limitation, closed cell foam) or cushioning material, the thickness of which is typically dictated by the part of the body that is being protected by the skin covering of the present invention.

Still referring to FIG. 3, outer layer 40 of protective skin covering 10 of the present invention typically comprises a durable, flexible, material (such as, for example, nylon or other similar material). In the preferred embodiment, said outer layer 40 provides a surface for decorative designs or other attractive features. In the preferred embodiment of the present invention, outer layer 40 is not directly affixed, stitched or joined with middle layer 30, except at or near the edges of said middle layer 30. Further, said inner layer 20 is likewise attached or connected to middle layer 30 at or near the outer perimeter of said middle layer 30. As a result, middle layer 30 is movably connected to both inner layer 20 and outer layer 40, and is thus able to "float" between inner layer 20 and outer layer 40. Further, because middle layer 30 and inner layer 20 are movably connected to one another, and because middle layer 30 and outer layer 40 are likewise movably connected to one another, middle layer 30 can slide or move laterally relative to both inner layer 20 and outer layer 40 when contact is made with a foreign object.

Figure 4:
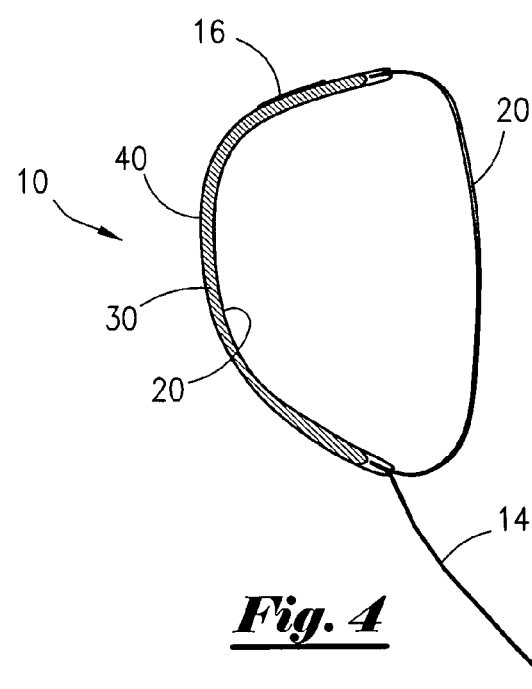
FIG. 4 depicts a cross-sectional view of the protective skin covering of the present invention depicted in FIG. 2 along line 4-4 of FIG. 2.

FIG. 4 depicts a cross-sectional view of the protective skin covering 10 of the present invention depicted in FIG. 2 along line 4-4 of FIG. 2. Inner layer 20 of protective skin covering 10 of the present invention forms a sleeve designed to substantially surround a user's forearm, and is constructed of soft, non-abrasive fabric. Middle layer 30 of protective skin covering 10 of the present invention comprises padding to protect a user's forearm from impact with foreign objects. Outer layer 40 of protective skin covering 10 of the present invention typically comprises a durable, flexible, material (such as, for example, nylon or other similar material). In the preferred embodiment, said outer layer 40 shields middle layer 30 and provides a surface for decorative designs or other attractive features. Lower straps 14 are disposed along one side of said sleeve section 11, and hook members 15 are disposed on said lower straps 14. Mating loop members 16 are disposed on the outer surface of sleeve section 11.

Figure 5:
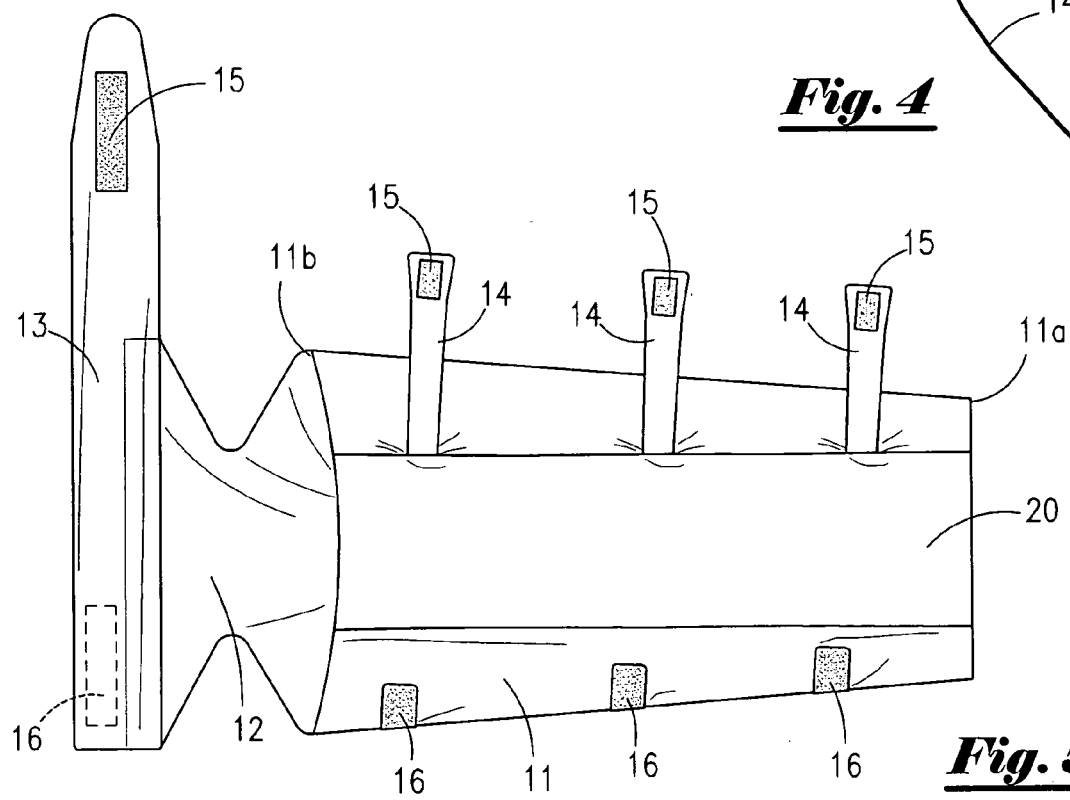
FIG. 5 depicts a bottom view of an opened protective skin covering of the present invention for use on a forearm.

FIG. 5 depicts a bottom view of a protective skin covering 10 of the present invention. Lower sleeve section 11, having forward end 11a and back end 11b, is generally sized to fit over and substantially cover the entire forearm of a user. As such, sleeve section 11 is of sufficient length to extend substantially the entire distance from a user's elbow area to said user's wrist area. Further, in the preferred embodiment, sleeve section 11 extends around the entire circumference of a user's forearm. In the preferred embodiment, sleeve section 11 is narrower at forward end 11a (which, when in use, is positioned in proximity to a user's wrist) and wider at back end 11b (which, when in use, is positioned in proximity to a user's elbow) to accommodate changes in thickness of a user's forearm area. In the preferred embodiment, the under surface of sleeve section 11 is constructed of inner layer material 20.

Still referring to FIG. 5, flap 12 is connected to back end 11b of sleeve section 11. In the preferred embodiment, flap 12 narrows inward toward its center to form a "neck-like" configuration. When protective skin covering 10 of the present invention is worn, flap 12 is positioned in general alignment with the outer surface of a user's elbow. Upper strap 13 is connected to flap 12. When in use, upper strap 13 is positioned in general proximity to a user's upper arm or bicep area.

Lower straps 14 are disposed along one side of said sleeve section 11. Hook members 15 are disposed on the end of lower straps 14, as well as upper strap 13. Mating loop members 16 are disposed on the outer surface of sleeve section 11 and upper strap 13. Upper strap 13 and lower straps 14 can be selectively loosened or tightened to adjust the tightness of said protective skin covering on a user's arm.

Figure 6:
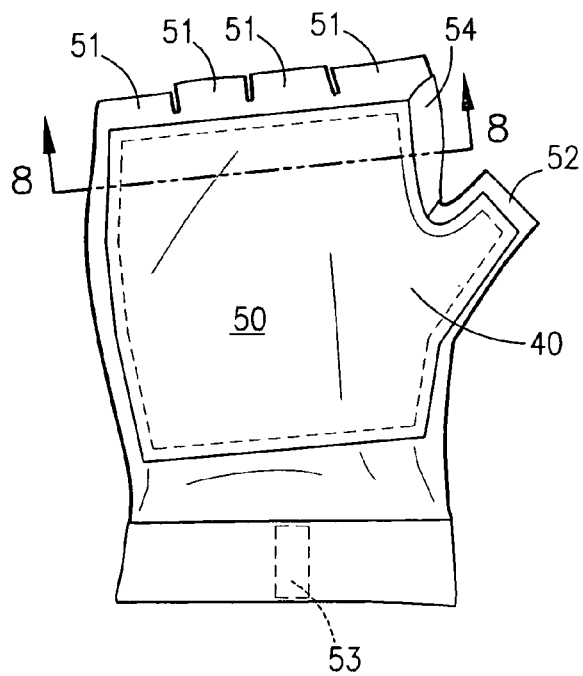
FIG. 6 depicts a side view of the back of a protective skin covering of the present invention configured to be worn on a left hand.

FIG. 6 depicts a side view of the back of a protective skin covering 50 of the present invention. In the preferred embodiment, protective skin covering 50 has the basic shape of a truncated glove—that is, a plurality of finger receptacles 51 and thumb receptacle 52. Like protective skin covering 10 designed for the arm of a user, protective skin covering 50 of the present invention comprises three distinct layers: inner layer 20 (which is disposed directly against the skin of a user), middle layer 30, and outer layer 40.

Figure 7:
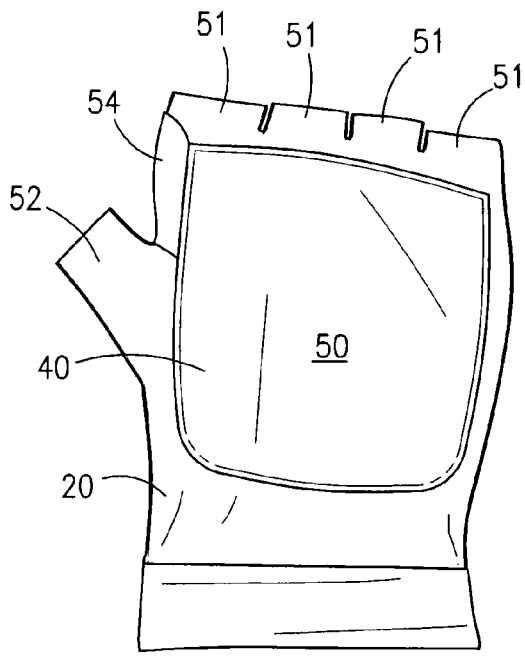
FIG. 7 depicts a side view of the palm of a protective skin covering of the present invention configured to be worn on a left hand.

In the preferred embodiment, inner layer 20 of the present invention forms the basic configuration of a truncated glove. Middle layer 30 of the present invention (not visible in FIG. 6) comprises padding to protect a user's hand from impact with foreign objects. In the preferred embodiment, said middle layer 30 generally comprises foam or cushioning material, the thickness of which is typically dictated by the part of the body that is to be covered. Outer layer 40 of the present invention typically comprises a durable, flexible material (such as, for example, nylon or other similar material). Durable material 54 (which can be the same material as durable outer layer 40) is disposed between the thumb receptacle 52 and finger receptacle 51 to reinforce such area. Hook member 53 is provided for use with mating loop member 17 of covering 10 (depicted in FIG. 2) to beneficially connect protective skin covering 50 to an adjacent protective skin covering 10 during use. FIG. 7 depicts a side view of the palm of protective skin covering 50 of the present invention; outer layer 40 is disposed adjacent to the palm section of said glove-like element.

In the preferred embodiment of the present invention, outer layer 40 is affixed, stitched or joined with middle layer 30 only at or near the outer perimeter of middle layer 30. Said inner layer 20 is likewise attached or connected to middle layer 30 only at or near the outer perimeter of said middle layer 30. As a result, outer layer 40 and inner layer 20 can both slide or move laterally relative to middle layer 30 when contact is made with a foreign object.

Figure 8:
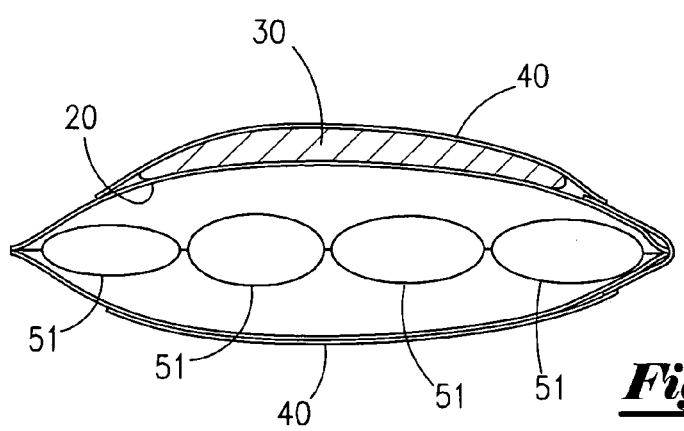
FIG. 8 depicts a cross-sectional view of the protective skin covering of the present invention depicted in FIG. 6 along line 8-8 of FIG. 6.

FIG. 8 depicts a cross-sectional view of protective skin covering 50 of the present invention depicted in FIG. 6 along line 8-8 of FIG. 6. Inner layer 20 of the present invention forms the basic configuration of a truncated glove. Middle layer 30 of the present invention comprises padding to protect the back of a user's hand from impact with foreign objects. In the preferred embodiment, said middle layer 30 generally comprises foam or cushioning material; said middle layer 30 has greater thickness along the outside of covering 50 (that corresponds to the back of a user's hand) because of the lack of natural muscle and/or fat tissue in that area. Outer layer 40 of the present invention typically comprises a durable, flexible material (such as, for example, nylon or other similar material) disposed on the palm and back of member 50.

In the preferred embodiment, the protective skin covering of the present invention is lightweight, inexpensive, foldable, roll-able and fully washable. Said protective skin covering can be used to safely protect damaged or sensitive skin during any number of different activities including, without limitation, every-day activities. The specific configurations described herein are illustrative only, and are not intended to represent an exhaustive list of all possible configurations of the present invention, or all parts of the human body that could benefit from the protective skin covering of the present invention.

As set forth above, an advantage of the present invention is that it draws moisture (such as perspiration) away from the skin of a user. Said inner and middle layers exhibit such "wicking" ability. In most applications, it is beneficial for the outer layer to also exhibit such wicking ability. However, in an alternative embodiment of the present invention, such outer layer may exhibit less wicking ability, and may be constructed of a harder, less permeable material.

The above-described invention has a number of particular features that should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:

1. A protective skin covering comprising:
   a. an inner sleeve, adapted to be disposed against the skin, having a first end and a second end, wherein said first end is narrower than said second end;
   b. an outer covering;
   c. a middle layer, disposed between said inner sleeve and outer covering, wherein said inner sleeve is movably connected to said middle layer;
   d. a flap attached to said second end of said sleeve;
   e. a strap, attached to said flap, having a first end and a second end; and
   f. at least one fastener for securing said first end of said strap to said second end of said strap.

2. The protective skin covering of claim 1, wherein said at least one fastener comprises at least one hook and loop fastener.

3. A protective skin covering comprising:
   a. an absorbent inner layer adapted to be disposed against the skin, wherein said inner layer is substantially in the form of a truncated glove;
   b. an outer layer; and
   c. a middle layer, disposed between said inner layer and outer layer, wherein said inner layer is movably connected to said middle layer.

4. The protective skin covering of claim 3, wherein said outer layer is movably connected to said middle layer.

5. The protective skin covering of claim 3, wherein said inner layer comprises a non-abrasive fabric.

6. The protective skin covering of claim 3, wherein said inner layer comprises a hypoallergenic fabric.

7. The protective skin covering of claim 3, wherein said inner layer has stitched seams oriented away from the skin.

8. The protective skin covering of claim 3, wherein said middle layer comprises cushioning material.

9. The protective skin covering of claim 8, wherein said cushioning material comprises closed cell foam.

10. The protective skin covering of claim 3, wherein said outer layer is durable and flexible.

11. The protective skin covering of claim 3, wherein said inner layer is capable of wicking moisture away from the skin.

12. The protective skin covering of claim 3, wherein said middle layer is capable of wicking moisture away from said inner layer.

13. The protective skin covering of claim 3, wherein said inner layer is anti-bacterial.

* * * * *